United States Patent [19]

Swisher

[11] Patent Number: 4,929,244
[45] Date of Patent: May 29, 1990

[54] BAFFLE SYSTEM FOR USE IN UNDERWATER DRAINAGE DEVICES

[75] Inventor: David R. Swisher, St. Louis, Mo.

[73] Assignee: Sherwood Medical Company, St. Louis, Mo.

[21] Appl. No.: 240,317

[22] Filed: Sep. 2, 1988

[51] Int. Cl.$^5$ .............................................. A61M 1/00
[52] U.S. Cl. ...................................... 604/319; 604/321
[58] Field of Search ...................... 604/317, 319–321, 604/323; 137/205; 128/760

[56] References Cited

U.S. PATENT DOCUMENTS

| | | | |
|---|---|---|---|
| 3,559,647 | 2/1971 | Bidwell et al. | 128/276 |
| 3,683,913 | 8/1972 | Kurtz et al. | 128/276 |
| 3,847,152 | 11/1974 | Schachet | 128/276 |
| 3,861,390 | 1/1975 | Schachet | 128/276 |
| 3,924,624 | 12/1975 | Schachet | 128/276 |
| 4,372,336 | 2/1983 | Cornell et al. | 137/205 |
| 4,430,085 | 2/1984 | Ahrens | 604/321 |
| 4,439,190 | 3/1984 | Protzmann et al. | 604/319 |
| 4,453,937 | 6/1984 | Kurtz et al. | 604/319 |
| 4,544,370 | 10/1985 | Elliott et al. | 604/319 |
| 4,619,647 | 10/1986 | Kurtz et al. | 604/318 |
| 4,655,754 | 4/1987 | Richmond et al. | 604/323 |
| 4,715,856 | 12/1987 | Elliott et al. | 604/321 |
| 4,747,843 | 5/1988 | Felix et al. | 604/318 |
| 4,747,844 | 5/1988 | Elliott | 604/319 |
| 4,781,707 | 11/1988 | Boehringer et al. | 604/319 |

OTHER PUBLICATIONS

Brochure: "Compact 2000", Codman & Shurtleff, Inc., Randolph, MA 02368.

*Primary Examiner*—Jerome L. Kruter
*Attorney, Agent, or Firm*—Andrew J. Beck; Montgomery W. Smith; Richard D. Allison

[57] ABSTRACT

An improved underwater drainage device having a baffle system preferably incorporated into the water seal column positioned in flow communication with the patient's pleural cavity wherein the baffle chamber consists of a baffle insert having a baffle tube and a plurality of spaced downwardly directed baffles. And wherein the baffle tube of the present invention includes a tapered outer wall directed toward the first baffle and sidewalls having a plurality of side openings to allow the water seal to flow downwardly therethrough once the negative pressure from the patient's pleural cavity has dissipated.

22 Claims, 3 Drawing Sheets

BAFFLE SYSTEM FOR USE IN UNDERWATER DRAINAGE DEVICES

FIELD OF THE INVENTION

This invention relates to underwater drainage devices and more particularly to an improved baffle system for use in protecting against the loss of the water seal during periods of high negative pressure in the patient's pleural cavity.

BACKGROUND OF THE INVENTION

Drainage devices for removing fluids from the pleural cavity of a patient generally include a collection chamber, an underwater seal chamber and a liquid pressure control or regulating manometer which limits the negative pressure applied to the collection chamber. Fluid from the patient's pleural cavity is drawn into and accumulated in the collection chamber while gas and air from the pleural cavity are drawn through the liquid seal in the underwater seal chamber and into the source of suction. The liquid seal acts as a barrier to prevent the patient's pleural cavity from being exposed to atmospheric pressure and also prevents the patient's pleural cavity from being in direct flow communication with the source of suction. The background and operation of underwater drainage devices is discussed more fully in U.S. Pat. No. 4,439,190, issued to Protzmann et al on Mar. 27, 1984, which is incorporated herein by reference.

Under certain conditions, prior drainage devices have experienced the loss of their water seal due to sudden surges or even gradual increases in the negative pressure in the patient's pleural cavity. This may occur when the patient gasps for air or when the drainage unit is being used as part of an autotransfusion device. During the typical operation of an underwater drainage device, when the patient inspires, the liquid will move upwardly in the water seal column. As the patient expires, the negative pressure in the patient's pleural cavity decreases and the water moves downwardly in the water seal column. If the patient suddenly gasps for air such as when there is a blockage in the patient's bronchial tubes, the negative pressure in the patient's pleural cavity will dramatically increase. This sudden increase in negative pressure in the patient's pleural cavity will force the liquid in the water seal column to surge upwardly and, often times, the liquid will flow into the collection chamber, thus depleting the water seal.

Another cause for the loss of the water seal in the underwater drainage device may occur during a process known as autotransfusion. During autotransfusion, blood is suctioned from the patient's pleural cavity and stored in a collection bag attached to the side of and connected for suction to the suction inlet of the drainage device. When this blood is needed, the collection bag is attached to an I.V. and the stored blood is pumped back into the patient. As the blood is pumped back into the patient, the negative pressure in the patient's plerual cavity and the negative pressure in the collection chamber of the drainage unit will gradually increase. This increase in the negative pressure in the patient's pleural cavity causes the liquid in the water seal to be drawn upwardly into the water seal column. Once all of the liquid from the water seal is drawn upwardly into the water seal column, air will begin bubbling through the bottom of the column. As the bubbling occurs, liquid from the water seal passes into the collection chamber. Once the water seal is lost, the patient's pleural cavity will be in direct flow communication with the suction source and also to the atmospheric pressure as air from the atmosphere is drawn into the drainage device through the manometer chamber.

One approach to the problem of losing the water seal during sudden pressure changes is disclosed in U.S. Pat. No. 3,861,290, issued to Schachet on Jan. 21, 1975. The Schachet drainage device provides a secondary liquid seal incorporating a valve which permits a restricted flow of liquid during periods of high negative pressure from the patient's pleural cavity while permitting an unrestricted flow of liquid and gas in the opposite direction. Another approach is illustrated in the aforementioned Protzmann patent. The Protzmann patent discloses the use of a restrictive passageway consisting of a limited number of horizontally aligned baffles in the manifold.

Despite these and other underwater drainage devices which restrict the flow of the water seal, a need remains for an improved drainage device which will allow gas to flow through the water seal freely in both directions and will prevent the water seal from being lost or depleted during sudden or gradual changes in the negative pressure of the patient's pleural cavity.

SUMMARY OF THE PRESENT INVENTION

It is therefore an object of the present invention to provide an improved underwater drainage device wherein the above mentioned disadvantages are substantially obviated.

Another object of the present invention is to provide an improved underwater drainage device having a simple and effective means for preventing the water seal from flowing into the collection chamber.

In accordance with one form of the present invention, the improved underwater drainage device is of the type of drainage device typically known as the three-bottle drainage device. Thus, the improved underwater drainage device of the present invention includes a collection chamber adapted to be in fluid communication with the patient's pleural cavity; an underwater seal chamber in flow communication with the collection chamber; and a manometer chamber. Additionally, the preferred embodiment of the present invention includes a manifold which maintains the various chambers in flow communication with each other.

The underwater seal chamber of the present invention includes an upper baffle chamber located in the water seal column. The baffle chamber is designed to allow bubbling in the water seal column without a loss of liquid from the water seal. The baffle chamber preferably includes a plurality of baffles oriented to obstruct the upward flow of air and liquid in the water seal from the water seal column. Additionally, as the negative pressure in the patient's pleural cavity subsides, the liquid will return to its normal position in the underwater seal chamber through a pair of openings located on the bottom surface of the baffle chamber.

DETAILED DESCRIPTION OF THE PREFERRED EMBODIMENT

Figure 1:
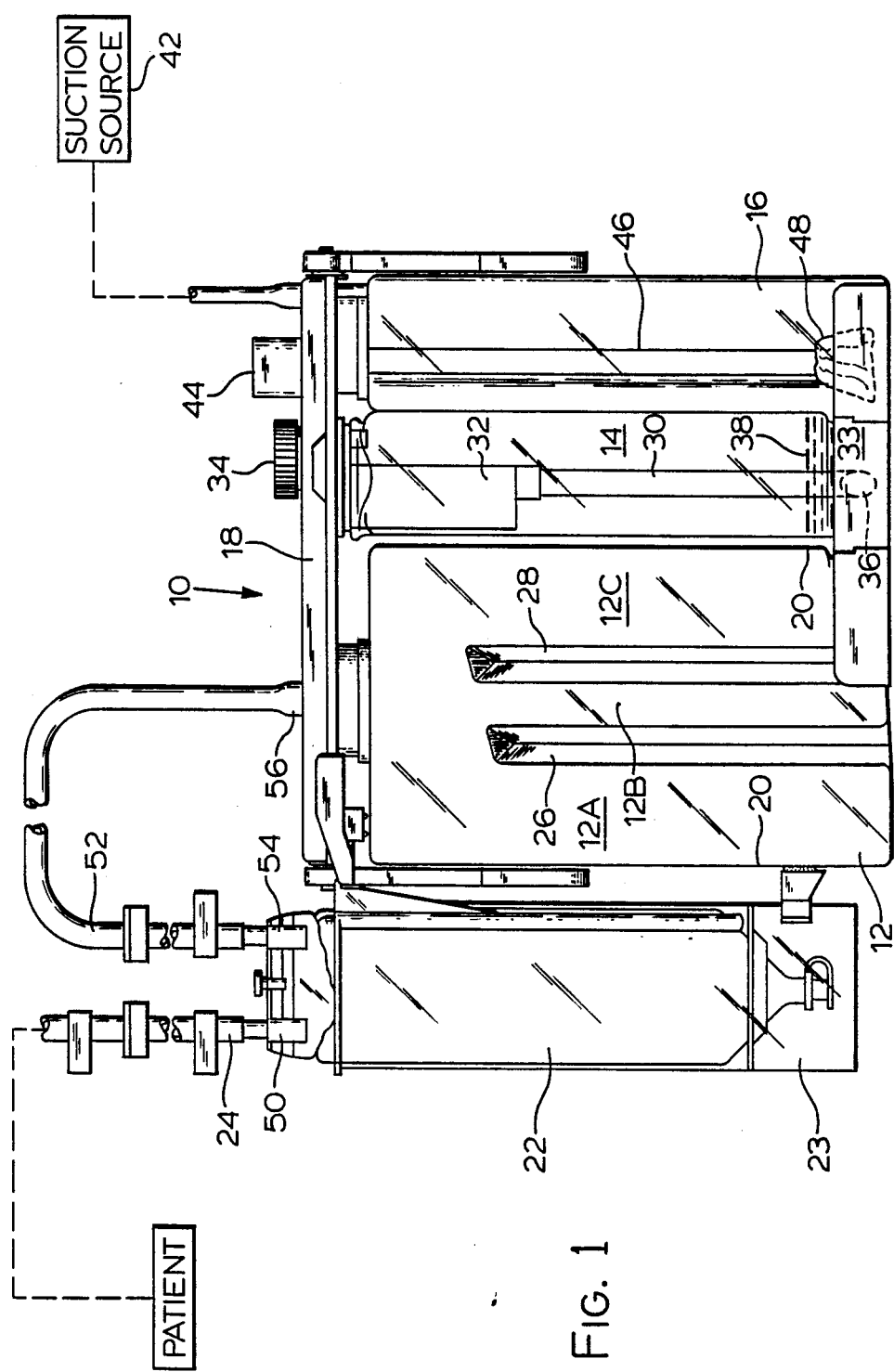
FIG. 1 is a cross-sectional side view of the present invention adapted for use during autotransfusion.
Figure 2:
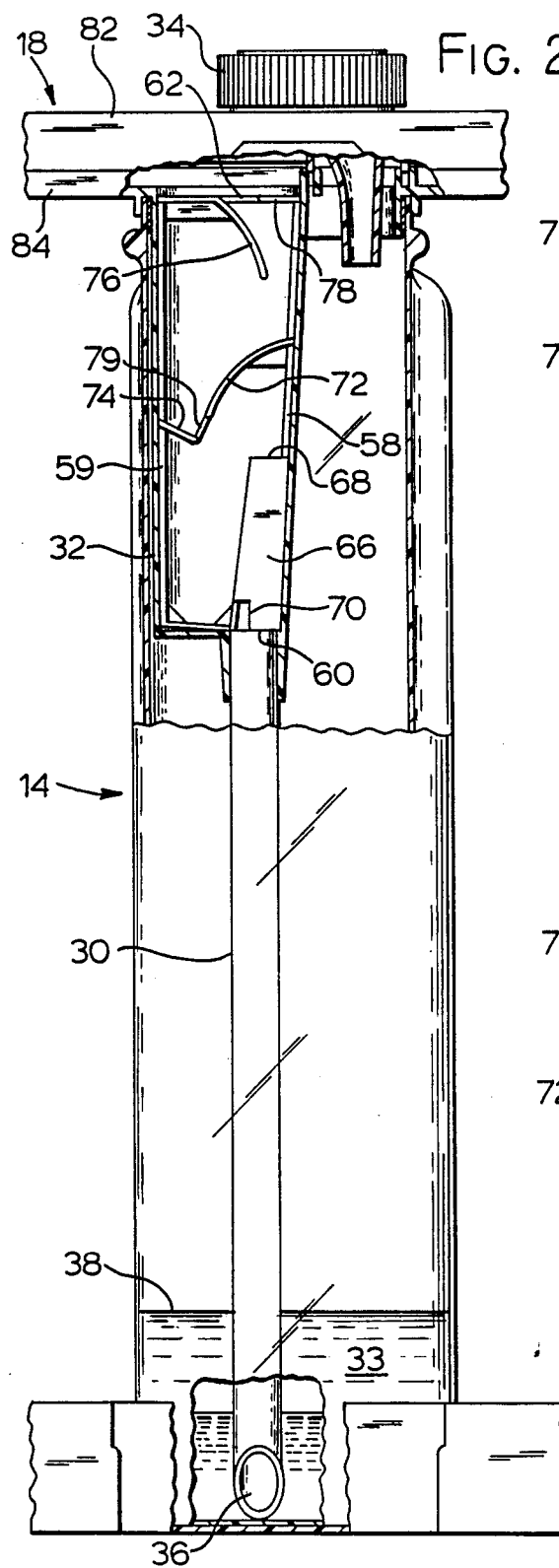
FIG. 2 is an enlarged cross-sectional view of the underwater seal chamber of the present invention.
Figure 3:
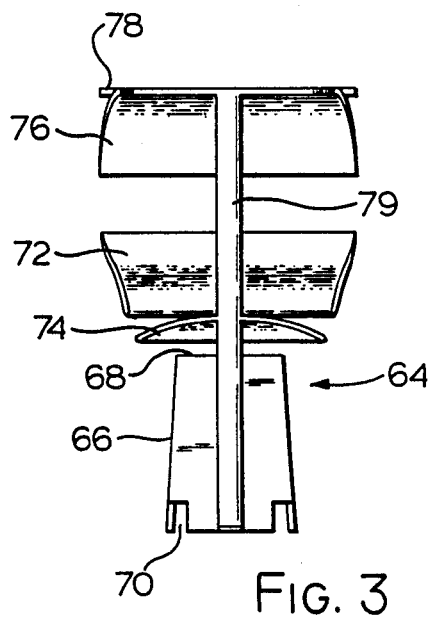
FIGS. 3 and 4 are side views of the baffle insert of the present invention.
Figure 4:
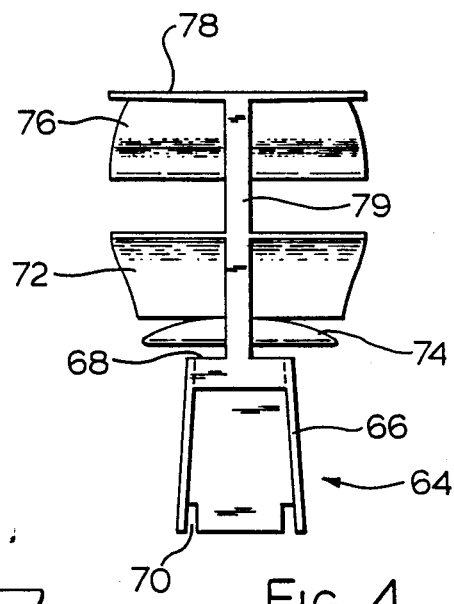
Figure 6:
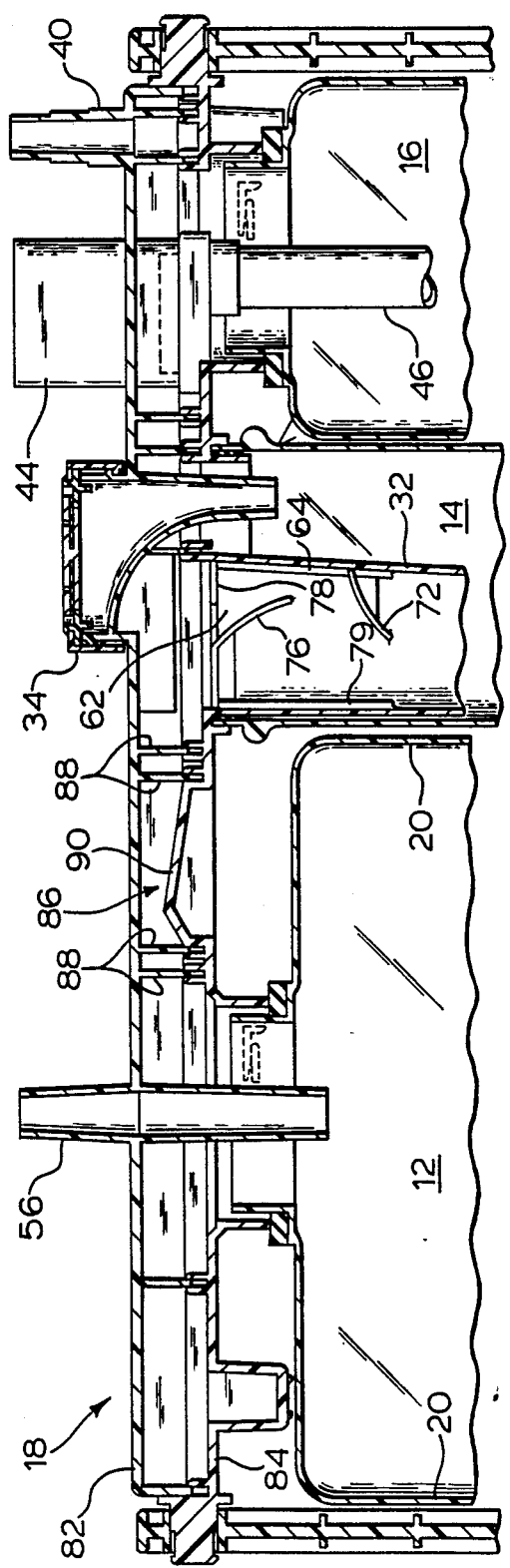
FIG. 6 is a side view in a partially cut-away, of the manifold of the present invention.

The preferred design of the present invention is illustrated in the attached drawings and is designated herein, generally, as a drainage device 10. The drainage device 10 of the present invention consists generally of a collection chamber 12, an underwater seal chamber 14, a manometer chamber 16 and a manifold 18. Additionally, FIG. 1 illustrates an autotransfusion collection bag 22 and collection bag holder 23 attached to the side of the drainage device 10. In the preferred embodiment, the manifold 18 is attached to the top of the collection chamber 12, and the manometer chamber 16 is attached to the manifold 18 adjacent to the underwater seal chamber 14. The manifold 18 provides the desired fluid communication between the collection chamber 12, the underwater seal chamber 14 and the manometer chamber 16, thus, eliminating the need for hoses, conduits and the like frequently used in various other underwater drainage devices.

In order to provide accurate measurement of the fluid collected from the patient's pleural cavity, the collection chamber 12 is provided with inner walls 26 and 28, which, in combination with the outer walls 20, divide the collection chamber 12 into three compartments 12a, 12b, and 12c. The height of wall 26 is less than the height of wall 28 so that once compartment 12a is filled, fluid will flow into compartment 12b. After compartment 12b is filled, fluid will spill over into compartment 12c. Each compartment has graduations thereon so that the attending physician or nurse can determine at a glance the amount of drainage from the patient's pleural cavity.

The underwater seal chamber 14 includes a water seal column 30 and a baffle chamber 32. Liquid is poured into the underwater seal chamber 14 through the fill cap 34 until it reaches the fill line indicated on the side of the underwater seal chamber 14. The volume of liquid placed in the underwater seal chamber 14 should be sufficient to continuously cover the bottom opening 36 of the water seal column 30 during the typical operation of the drainage device 10. This volume of liquid is known generally as the water seal and is referred herein as the water seal 38.

The manometer chamber 16 is of a generally standard design and includes a vacuum hose 40 attached to its top end which is connected to the vacuum source 42. The top end of the manometer chamber 16 also includes a fill opening 44 which is open to the atmosphere and allows liquid to be poured into the manometer chamber 16. The interior of the manometer chamber 16 further includes a tube 46 which extends downwardly from the fill opening 44 to a lower membrane 48. The lower member 48 muffles the noise caused by the drainage device 10 when air enters the manometer chamber 16 through the tube 46.

Figure 5:
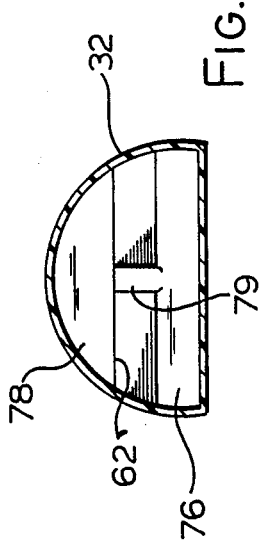
FIG. 5 is a top view of the baffle insert of the present invention.

The manifold 18 consists of a variety of openings and passageways to interconnect the collection chamber 12, the underwater seal chamber 14 and the manometer chamber 16 with the vacuum source 42 and pleural cavity of the patient. As illustrated in FIG. 5, the manifold 18 consists of separate top and bottom halves 82 and 84, respectively, which are joined together in a fluid tight manner. The top and bottom halves 82 and 84, respectively, form a restrictive passageway 86 between the underwater seal chamber 14 and the collection chamber 12. In this embodiment, the restrictive passageway 86 is formed by four ridges 88 which alternately extend from the front and back sides of the manifold 18. A slanted ridge 90 is also positioned between the two inner most baffles 86 to further restrict the flow of fluid from the underwater seal chamber 14 to the collection chamber 12 if the drainage device 10 is inadvertently tipped or placed on its side. The restrictive passageway 86 also operates as a backup baffle system to the baffle chamber 32 in the event that unusually high negative pressures are encountered in the patient's pleural cavity or if the underwater seal chamber 14 is improperly filled.

The baffle chamber 32 consists of elongate opposing sidewalls 58 and 59, a bottom opening 60 and a top opening 62. The baffle chamber 32 also houses the baffle insert 64 which includes a tapered baffle tube 66 having a top baffle opening 68 and side baffle openings 70, and a plurality of downwardly directed baffles, 72, 74, 76 and 78. A downwardly curved first baffle 72 is positioned along the first sidewall 58 immediately above the top baffle opening 68. This first baffle 72 extends beyond the middle of the baffle chamber 32 as defined by the first and second sidewalls 58 and 59. A second baffle 74 is positioned along the second sidewall 59 and extends beneath the lower end of the first baffle 72. A third downwardly curved baffle 76 is positioned along the second sidewall 59 above the top ends of the first and second baffles 72 and 74, respectively. The third baffle 76 extends beyond the midpoint of the baffle chamber 32. Finally, a fourth baffle 78 is positioned perpendicular to the first sidewall 58 near the top opening 62 of the baffle chamber 32. The fourth baffle 78 is oriented with the top end of the third baffle 76 to provide a restrictive outlet for the flow of air through the top opening 62 of the baffle chamber 32. The baffles 72, 74, 76 and 78 are interconnected by a plurality of support struts 79 which extend along the sidewalls 58 and 59, the bottom opening 60 and the top opening 62 of the baffle chamber 32 to create the baffle insert 64 which, in the preferred embodiment, is press fit into the preformed baffle chamber 32.

During autotransfusion, a collection bag 22 and collection bag holder 23 are releasably attached to the side of the drainage device 10. A drainage tube 24 is attached from the patient's pleural cavity to the inlet 50 on the collection bag 22 and the vacuum tube 52 is attached from the collection bag outlet 54 to the inlet 56 on the manifold 18. Once the collection bag 22 is attached to the drainage device 10, the collection bag 22 functions essentially as a flexible collection chamber to collect blood from the patient as it is drained from the patient's pleural cavity. Once the collection bag 22 is full, the excess fluid from the pleural cavity will flow into the collection chamber 12 through the vacuum tube 52. When the doctor determines that it is necessary to reinfuse the collected blood into the patient, the drainage tube 24 and the vacuum tube 52 are clamped shut and the collection bag 22 is removed. The collection bag 22 is then attached to an intravenous administration set and the collected blood is reinfused into the patient. While the blood is reinfused into the patient, a second collection bag (not shown) may be attached to the drainage device 10 and further fluid is removed from the patient's pleural cavity. Under certain circumstances, the autotransfusion process is performed using only one collection bag 22. When this type of autotransfusion is used, the intravenous administration set is attached directly to the bottom of the collection bag 22 and the blood is pumped from the bottom of the collection bag 22 at the same time as blood is being suctioned into the top of the collection bag 22.

The drainage device 10 of the present invention functions similar to other drainage devices under normal operating conditions. Initially, a predetermined amount of liquid is added to the underwater seal chamber 14 to create the water seal 38. Liquid is also added to the manometer chamber 16 to a level corresponding to the prescribed suction pressure. Once the vacuum hose 40 is attached to the vacuum source 42 and the drainage tube 24 is attached to the patient's pleural cavity, the process of suctioning fluid from the patient's pleural cavity is begun. If the vacuum pressure from the vacuum source 42 exceeds the patient suction level, atmospheric air will be drawn into the manometer chamber 16 through the fill opening 44 and tube 46 to decrease the suction pressure being applied to the patient's pleural cavity. In the underwater seal chamber 14, the water seal 38 is drawn upwardly into the water seal column 30 whenever the patient inspires (negative pressure). The liquid will flow downwardly in the water seal column 30 and into the reservoir area 33 of the underwater seal chamber 14 whenever the patient breathes out (positive pressure). As the fluid is drawn from the patient's pleural cavity, the pleural cavity fluid is collected in the collection bag 22 or the collection chamber 12 and any air drawn from the patient's pleural cavity will flow through the underwater seal chamber 14 and into the vacuum source 42.

Whenever there is a sudden change in the pressure in the patient's pleural cavity, the liquid in the water seal 38 will surge upwardly or downwardly in response to this sudden pressure change. If there is a blockage in the patient's bronchial tubes, a sudden negative pressure will be created in the patient's pleural cavity and the liquid in the water seal 38 will be drawn upwardly into the water seal column 30. The liquid is drawn upwardly until the bottom opening 36 is exposed to the air in the underwater seal chamber 14. When this occurs, the air will bubble upwardly through the water seal column 30 and both the air and liquid will begin to bubble into the baffle chamber 32.

Whenever bubbling occurs in the baffle chamber 32, the air and liquid will flow into the baffle chamber 32 through the top opening 68 of the baffle tube 66. The top end of the baffle tube 66 is tapered to direct the air and liquid to contact the first baffle 72. The curve of the first baffle 72 directs the air and liquid downwardly towards the bottom surface of the baffle chamber 32. The air and liquid will then splash upwardly and contact the shorter second baffle 74. The second baffle 74 once again directs the air and liquid downwardly towards the bottom of the baffle chamber 32. If the air and liquid are drawn above the first and second baffles 72 and 74, respectively, the air and liquid will contact the third baffle 76. The third baffle 76 partially obstructs the top opening 62 of the baffle chamber 32 to prevent the water seal 38 from passing into the manifold 18. If the air and liquid bypass the third baffle 76, the air and liquid will contact the fourth baffle 78. The fourth baffle 78 extends inwardly from the first sidewall 69 to further restrict the top opening 62 of the baffle chamber 32.

Finally, if any liquid passes through the baffle chamber 32, the liquid must flow through the restrictive passageway 86 in the manifold 18 before it enters the collection chamber 12.

Once the patient's high negative pressure subsides, the bubbling in the baffle chamber 32 will subside and any liquid in the baffle chamber 32 will flow downwardly through the side openings 70 on the baffle tube 66 and into the water seal column 30. The volume of the baffle chamber 32 is designed to accommodate the entire volume of liquid from the water seal 38 and approximately one and one-half times the volume of liquid capable of being drawn upwardly into the water seal column 30. Additionally, the total volume of the baffle chamber 32 and manifold 18 are designed to accommodate nearly twice the volume of liquid from the water seal 38 capable of being drawn into the water seal column 30. This excess volume, and the use of the obstructive baffles in the baffle chamber 32 and manifold 18 insure that the water seal 38 will not be lost during the dramatic pressure changes which may occur in the patient's pleural cavity.

The baffle chamber 32 of the present invention is also particularly designed to accommodate the gradual pressure changes which occur during autotransfusion. During autotransfusion, the collection bag 22 is initially attached to the drainage device 10 to collect the blood from the patient's pleural cavity. When the doctor or nurse determines that this blood should be infused into the patient, the collection bag 22 is connected to an I.V. and the blood is reinfused into the patient. During the reinfusion process, the blood is typically pumped into the patient either from the bottom of a collection bag 22 which is still attached to the drainage device 10 or from a collection bag 22 which has been removed from the drainage device 10 and suspended above the patient. This additional pumping of blood into the patient causes a gradual increase in the negative pressure in the patient's pleural cavity. This gradual increase in the negative pressure draws the water seal 38 upwardly into the water seal column 30. Periodically, the drainage device 10 will adjust the pressure between the patient's pleural cavity and the vacuum source 42 by bubbling air and liquid from the water seal 38 through the water seal column 30. In a typical drainage device, this bubbling will gradual deplete the water seal 38. In the present invention, the water seal 38 is drawn upwardly into the baffle chamber 32 where the bubbling may safely occur without the loss of liquid from the water seal 38.

While the preferred form of the invention has been described with reference to one specific type of drainage device, it will be apparent that various changes and modifications thereto may be made without departing from the true scope of the invention as defined in the claims which follow. Particularly, the baffle insert 64 is designed to be readily adaptable for use in a variety of drainage devices with only minor modification thereto.

What is claimed is:

1. An underwater drainage device for removing liquids and gases from the body of a patient comprising,
   a first collection chamber in flow communication with the body of a patient wherein fluid from the patient will be suctioned into the first collection chamber,
   an underwater seal chamber having a predetermined amount of liquid therein and wherein the underwater seal chamber is in flow communication with the first collection chamber, a source of negative suction pressure in flow communication with the underwater seal chamber, a means for providing the flow communication between the first collection chamber, the underwater seal chamber and the source of suction, said underwater seal chamber including a water seal column and an upper baffle chamber wherein, as the pressure in the first collection chamber decreases below the regulated suction pressure from the suction source, the liquid in the underwater seal chamber will be drawn upwardly through the water seal column into the upper baffle chamber, the baffle chamber further having a volume greater than the predetermined volume of liquid capable of being drawn into the water seal column and said baffle chamber including a top and bottom end and opposed sidewalls, a plurality of baffles spaced along and extending from the sidewalls of said baffle chamber to obstruct the flow of liquid through the baffle chamber, and wherein the bottom end of said baffle chamber includes a baffle tube extending upwardly therefrom and having top and bottom ends aligned in flow communication with the water seal column wherein said bottom end of said baffle tube has a bottom opening therein having a larger area than the top opening on said top end of said baffle tube.

2. The underwater drainage device of claim 1, wherein the baffle tube is tapered and includes a drainage opening therein to allow liquid to flow from said baffle chamber into said water seal column.

3. An underwater drainage device for removing liquids and gases from the body of a patient comprising, a first collection chamber in flow communication with the body of a patient wherein fluid from the patient will be suctioned into the first collection chamber, an underwater seal chamber having a predetermined amount of liquid therein and wherein the underwater seal chamber is in flow communication with the first collection chamber, a source of negative suction pressure in flow communication with the underwater seal chamber, a means for providing the flow communication between the first collection chamber, the underwater seal chamber and the source of suction, said underwater seal chamber including a water seal column and an upper baffle chamber wherein, as the pressure in the first collection chamber decreases below the regulated suction pressure from the suction source, the liquid in the underwater seal chamber will be drawn upwardly through the water seal column into the upper baffle chamber, the baffle chamber further having a volume greater than the predetermined volume of liquid capable of being drawn into the water seal column and said baffle chamber including a top and bottom end and opposed sidewalls, a plurality of baffles spaced along and extending from the sidewalls of said baffle chamber to obstruct the flow of liquid through the baffle chamber, and wherein a plurality of baffles extend downwardly from the sidewalls of said baffle chamber beyond the middle of the baffle chamber as defined by the opposing baffle containing sidewalls of said baffle chamber.

4. The underwater drainage device of claim 3, wherein a further plurality of baffles extend from the sidewalls of said baffle chamber to a location less than the middle of the baffle chamber as defined by the opposing baffle containing sidewalls of said baffle chamber.

5. An underwater drainage device for removing liquids and gases from the body of a patient comprising, a first collection chamber in flow communication with the body of a patient wherein fluid from the patient will be suctioned into the first collection chamber, an underwater seal chamber having a predetermined amount of liquid therein and wherein the underwater seal chamber is in flow communication with the first collection chamber, a source of negative suction pressure in flow communication with the underwater seal chamber, a means for providing the flow communication between the first collection chamber, the underwater seal chamber and the source of suction, said underwater seal chamber including a water seal column and an upper baffle chamber wherein, as the pressure in the first collection chamber decreases below the regulated suction pressure from the suction source, the liquid in the underwater seal chamber will be drawn upwardly through the water seal column into the upper baffle chamber, the baffle chamber further having a volume greater than the predetermined volume of liquid capable of being drawn into the water seal column and said baffle chamber including a top and bottom end and opposed sidewalls, a plurality of baffles spaced along and extending from the sidewalls of said baffle chamber to obstruct the flow of liquid through the baffle chamber, and wherein a manifold includes a restrictive passageway therein to further restrict the fluid communication between the underwater seal chamber and the collection chamber.

6. The underwater drainage device of claim 5, wherein said means for providing the flow communication includes a restrictive passageway therein to further restrict the fluid communication between the underwater seal chamber and the collection chamber.

7. An underwater drainage device for removing liquids and gases from the body of a patient comprising, a first collection chamber in flow communication with the body of a patient wherein fluid from the patient will be suctioned into the first collection chamber, an underwater seal chamber having a predetermined amount of liquid therein and wherein the underwater seal chamber is in flow communication with the first collection chamber, a source of negative suction pressure in flow communication with the underwater seal chamber, a means for providing the flow communication between the first collection chamber, the underwater seal chamber and the source of suction, said underwater suction chamber including a water seal column and an upper baffle chamber wherein, as the pressure in the first collection chamber decreases below the regulated suction pressure from the suction source, the liquid in the underwater seal chamber will be drawn upwardly through the water seal column into the upper baffle chamber, the baffle chamber further having a volume greater than the predetermined volume of liquid capable of being drawn into the water seal column and said baffle chamber including a top and bottom end and opposed sidewalls, a plurality of baffles spaced along and extending from the sidewalls of said baffle chamber to obstruct the flow of liquid through the baffle chamber, and wherein the baffles are interconnected by a plurality of support struts to create a baffle insert which is removably positioned within said baffle chamber.

8. An underwater drainage device comprising a first collection chamber in flow communication with the pleural cavity of a patient to direct fluid from the pleural cavity of the patient to the first collection chamber, an underwater seal chamber containing a water seal consisting of a predetermined amount of liquid therein and wherein said underwater seal chamber includes a water seal column and an upper baffle chamber in flow communication with said first collection chamber, a pressure regulator having a variable level of liquid therein for regulating the suction pressure for removing fluid from the pleural cavity of a patient wherein the pressure regulator is in flow communication with the underwater seal chamber, a source of negative suction pressure flow communication with the underwater seal chamber and pressure regulator, said baffle chamber including top, bottom and first and second side surfaces wherein a baffle tube extends upwardly from the bottom surface of said baffle chamber in flow communication with the water seal column, and a plurality of baffles extending downwardly from the side surfaces of said baffle chamber wherein the baffles are oriented to obstruct the flow of liquid as the liquid passes from the baffle tube and through the baffle chamber.

9. The underwater drainage device of claim 8, wherein the baffles of said baffle chamber comprise a removable insert including a plurality of support struts interconnecting said baffles.

10. The underwater drainage device of claim 8, wherein the baffle tube is tapered and includes top, bottom and side surfaces wherein the top surface includes a restrictive outlet for directing fluid upwardly against one of said baffles and the side surface of said baffle tube includes a further opening therein for directing liquid from said baffle chamber into said water seal column.

11. The underwater drainage device of claim 8, wherein the volume of said baffle chamber is larger than the volume of liquid comprising the water seal.

12. The underwater drainage device of claim 8, wherein the baffle chamber includes opposingly oriented first and second side surfaces and wherein at least one baffle extends downwardly from each of the first and second side surfaces.

13. The underwater drainage device of claim 12, wherein the baffle tube is tapered and extends upwardly along the first side surface of said baffle chamber and a first baffle extends downwardly from said first side surface in flow communication with said tube and wherein a second baffle extends downwardly from said second side surface near the top surface of said baffle chamber.

14. The underwater drainage device of claim 12, wherein a third baffle extends from the first side surface near the top surface of said baffle chamber.

15. The underwater drainage device of claim 8, further including a second collection chamber oriented in flow communication between the pleural cavity of the patient and the first collection chamber to serve as a storage chamber as fluids are collected from the pleural cavity of the patient for subsequent reinfusion into the patient.

16. The underwater drainage device of claim 8, wherein the baffle chamber includes opposingly oriented first and second side surfaces wherein the first and second side surfaces include at least one downwardly curved baffle extending beyond the middle of the baffle chamber as defined by said first and second side surfaces of said baffle chamber.

17. The underwater drainage device of claim 16, wherein a further plurality of baffles extend outwardly from the first and second side surfaces of the baffle chamber a distance less than the middle of the baffle chamber as defined by said first and second side surfaces of said baffle chamber.

18. The underwater drainage device of claim 8, wherein the manifold includes a restrictive passageway for further restricting the flow of fluid from said underwater chamber into the collection chamber.

19. The underwater drainage device of claim 8, wherein the baffle tube is tapered to direct the air and liquid from the water seal column to contact a first downwardly curved baffle on said first surface and wherein the air and liquid will contact a second baffle on said second side surface and wherein the air and liquid will next contact a third baffle on said second side surface and wherein a fourth baffle on said first side surface is oriented adjacent to the top surface of said baffle chamber.

20. The underwater drainage device of claim 19, wherein a manifold having a restrictive passageway therein is located in flow communication between the baffle chamber and the pleural cavity of the patient.

21. A baffle chamber for use in an underwater drainage device having a collection chamber in flow communication with the body of a patient, a source of negative pressure and an underwater seal chamber containing a water seal column and a predetermined volume of liquid in the bottom section thereof, the baffle chamber comprising a top end and opposed sidewalls positioned above the water seal column in the underwater seal chamber, a plurality of baffles spaced along and extending inwardly from said opposed sidewalls of said baffle chamber, wherein a plurality of said baffles extend downwardly from said sidewalls of said baffle chamber beyond the middle of said baffle chamber as defined by the baffles on the opposed sidewalls of said baffle chamber, and the baffle chamber having a volume greater than the predetermined volume of liquid in the bottom section of the underwater seal chamber.

22. A baffle chamber for use in an underwater drainage device having a collection chamber, a source of negative pressure, a manometer chamber and an underwater seal chamber wherein the underwater seal chamber includes a water seal column in the bottom section thereof and including a predetermined amount of liquid therein and wherein the collection chamber, the manometer chamber and the underwater seal chamber are in flow communication with the body of a patient and the source of negative pressure, the baffle chamber comprising top and bottom ends and opposed sidewalls, a plurality of baffles spaced along and extending inwardly from said sidewalls of said baffle chamber wherein the baffles are curved to deflect liquid from the water seal column downwardly toward the bottom end of said baffle chamber in the underwater seal column, and wherein said baffle chamber has a predetermined volume greater than the predetermined amount of liquid in the underwater seal chamber.

* * * * *